US010485632B1

(12) United States Patent
Al-Ekrish et al.

(10) Patent No.: US 10,485,632 B1
(45) Date of Patent: Nov. 26, 2019

(54) INTRAORAL ATTACHMENT CLIP FOR ATTACHMENT OF OBJECTS TO EDENTULOUS RIDGES

(71) Applicant: KING SAUD UNIVERSITY, Riyadh (SA)

(72) Inventors: Asma'a Abdurrahman Al-Ekrish, Riyadh (SA); Shouq Abdullah Jurays, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/202,052

(22) Filed: Nov. 27, 2018

(51) Int. Cl.
| A61C 1/00 | (2006.01) |
| A61B 90/00 | (2016.01) |
| A61B 6/14 | (2006.01) |
| A61C 19/04 | (2006.01) |

(52) U.S. Cl.
CPC .............. *A61B 90/39* (2016.02); *A61B 6/145* (2013.01); *A61B 2090/3912* (2016.02); *A61B 2090/3966* (2016.02); *A61B 2090/3983* (2016.02); *A61B 2090/3991* (2016.02); *A61C 19/04* (2013.01)

(58) Field of Classification Search
CPC . A61B 90/39; A61B 6/145; A61B 2090/3912; A61B 2090/3966; A61B 2090/3983; A61B 2090/3991; A61C 8/0022; A61C 8/0006; A61C 8/0086; A61C 8/0034; A61C 5/80; A61C 2008/0046; A61C 19/04
See application file for complete search history.

(56) References Cited

U.S. PATENT DOCUMENTS

| 4,407,286 A | * | 10/1983 | Noiles | ............... A61B 17/0644 227/175.1 |
| 4,412,824 A | * | 11/1983 | Kulwiec | ............ A61C 13/0003 433/170 |
| 4,702,697 A | * | 10/1987 | Linkow | ............... A61C 8/0031 433/173 |

(Continued)

FOREIGN PATENT DOCUMENTS

WO    2017/081337 A1    5/2017

OTHER PUBLICATIONS

Yeshwante et al., "Mastering Dental Implant Placement: A Review" Journal of Applied Dental and Medical Sciences, vol. 3, issue 2, Apr.-Jun. 2017.

*Primary Examiner* — Nicholas D Lucchesi
(74) *Attorney, Agent, or Firm* — Richard C. Litman; Nath, Goldberg & Meyer

(57) ABSTRACT

The intraoral attachment clip for attaching objects to edentulous ridges has a flexible body configured as an elongated U-shaped strip that is designed to be conformed to an edentulous ridge. The clip has a lower or tissue surface adapted for contacting the mucosal surface of the ridge and an upper or oral surface facing the oral cavity. The tissue surface of the clip includes a plurality of micro-projections and an adhesive for securing the device to the underlying mucosal surface of the edentulous ridge. Tracking sensors and/or radiopaque fiducial markers can be attached to the oral surface of the clip for use with surgical navigation systems and imaging procedures. Sustained release drugs may be added to the tissue surface of the device for administering time-release medications through the mucosa over a prolonged period of time.

13 Claims, 3 Drawing Sheets

(56) References Cited

U.S. PATENT DOCUMENTS

| | | | | |
|---|---|---|---|---|
| 5,324,294 | A * | 6/1994 | Elia | A61B 17/064 606/76 |
| 6,217,594 | B1 * | 4/2001 | Hallen | A61B 17/0057 606/157 |
| 8,172,573 | B2 | 5/2012 | Sonenfeld et al. | |
| 8,246,974 | B2 * | 8/2012 | Chappa | A61K 9/0051 424/423 |
| 8,435,033 | B2 * | 5/2013 | Gross | A61C 1/084 433/214 |
| 8,529,939 | B2 | 9/2013 | Masters et al. | |
| 8,632,573 | B2 * | 1/2014 | Ellis | A61B 17/8076 606/280 |
| 9,084,635 | B2 | 7/2015 | Nuckley et al. | |
| 9,254,177 | B2 | 2/2016 | Stratton et al. | |
| 9,808,297 | B2 * | 11/2017 | Bernstein | A61B 17/808 |
| 10,080,615 | B2 | 9/2018 | Bartelme et al. | |
| 2003/0092957 | A1 | 5/2003 | Scott et al. | |
| 2003/0232308 | A1 * | 12/2003 | Simmons, Jr. | A61C 8/0031 433/173 |
| 2005/0032024 | A1 * | 2/2005 | Castellon | A61C 8/0048 433/172 |
| 2005/0033427 | A1 * | 2/2005 | Freilich | A61B 17/68 623/16.11 |
| 2005/0059864 | A1 * | 3/2005 | Fromovich | A61C 8/0033 600/201 |
| 2011/0165536 | A1 * | 7/2011 | Better | A61B 17/32 433/32 |
| 2012/0130421 | A1 * | 5/2012 | Hafez | A61B 17/0643 606/220 |
| 2016/0120582 | A1 * | 5/2016 | Martinez Navarro | A61C 8/0022 433/169 |
| 2016/0015781 | A1 | 6/2016 | Slak et al. | |
| 2016/0154468 | A1 * | 6/2016 | Kimmel | G08C 17/02 345/156 |
| 2017/0367806 | A1 * | 12/2017 | Gingras | A61L 31/005 |
| 2018/0078332 | A1 | 3/2018 | Mozes et al. | |

\* cited by examiner

INTRAORAL ATTACHMENT CLIP FOR ATTACHMENT OF OBJECTS TO EDENTULOUS RIDGES

BACKGROUND

1. Field

The disclosure of the present patent application relates to dental appliances, and particularly to an intraoral attachment clip for attaching objects to edentulous ridges.

2. Description of the Related Art

One method of implant placement in the dental field is through surgical navigation systems. A surgical navigation system is a system that provides real-time tracking of the drill, as well as the implant position and orientation during placement of the implant. It comprises a computer monitor, on which a radiographic image (MDCT\CBCT) of the area of interest is displayed, along with radiopaque fiducial markers placed on both the jaw and the drilling piece, and extraoral optical sensors equipped with cameras. The fiducial markers are placed during radiographic imaging and during the surgical procedure to allow registration of the position of the jaw in the surgical field to the position within the images. The fiducial markers are also necessary for tracking of the position of the drill in relation to the jaw.

Currently, one recommended technique for placement of the fiducial markers in long-span edentulous areas places fiducial markers on a bulky attachment connected to a metal implant drilled into the jaw and protruding into the oral cavity. The bulky attachment has to be worn during the imaging procedure. After imaging, the attachment is removed, but the metal implant remains in the bone until the navigation surgery. During the navigation surgery, the attachment with the fiducial markers is reconnected to the metal implant to allow registration of the fiducial markers to their position in the previously acquired images.

However, the technique is highly invasive, requiring drilling of bone. Also, due to the bulkiness of the attachment, it limits accessibility to the surgical field and reduces the patient's comfort. In addition, the fiducials are removed from the jaws after imaging and repositioned at the time of surgery. This repositioning may possibly lead to a change in the fiducials' relationship to the jaws during the surgery, as compared to their relationship in the images, thus leading to inaccurate position of the drilling. Finally, the plasticity of the attachment and its bulkiness may increase the risk of the operator's hands or instruments inadvertently applying pressure on the attachment during the surgery, which may also lead to inaccurate positioning of the drill.

Thus, an intraoral attachment clip for attaching objects to edentulous ridges solving the aforementioned problems is desired.

SUMMARY

The intraoral attachment clip for attaching objects to edentulous ridges has a flexible body configured as an elongated U-shaped strip that is designed to be conformed to an edentulous ridge. The clip has a lower or tissue surface adapted for contacting the mucosal surface of the ridge and an upper or oral surface facing the oral cavity. The tissue surface of the clip includes a plurality of micro-projections and an adhesive for securing the device to the underlying mucosal surface of the edentulous ridge. Radiopaque fiducial markers and tracking sensors can be attached to the oral surface of the clip for use with surgical navigation systems and imaging procedures. Sustained release drugs may be added to the tissue surface of the device for administering time-release medications through the mucosa over a prolonged period of time.

The intraoral attachment clip is noninvasive, causing less patient discomfort, and may be left in place between radiographic imaging and surgery, thereby reducing the risk of misalignment of fiducial markers during implant surgery.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
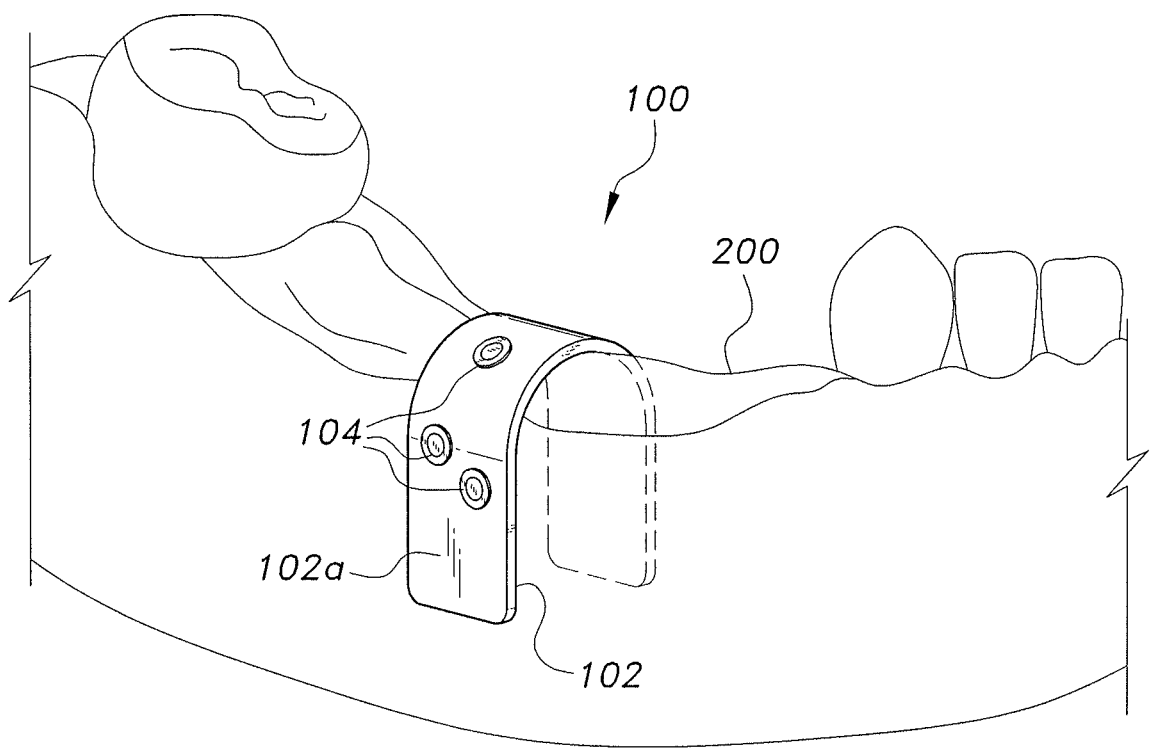
FIG. 1 is an environmental, perspective view of an intraoral attachment clip attached to an edentulous ridge.

The intraoral attachment clip 100 for attachment of objects to edentulous ridges is shown attached to a mandibular edentulous ridge 200 in FIG. 1. The body 102 of the clip 100 may be made from an elongated strip of a deformable material that is designed to be shaped by the practitioner during a procedure. The thickness of the body 102 is determined based on the flexibility of the material used to make the body 102. In a preferred embodiment, the body 102 is a semi-rigid U-shaped polymeric body of a thickness and malleability that allows the practitioner to place the clip 100 over the ridge and conform the clip to the patient's edentulous alveolar ridge 200 using only his/her fingers, and without causing damage to the mucosa of the ridge 200. Accordingly, the clip 100 can be manipulated to conform to the facial, crestal, or lingual mucosa of the edentulous ridge 200. The material of the clip 100 may be selected based its radiolucency, flexibility/adaptability, and capability of forming microprojections thereon.

Figure 2:
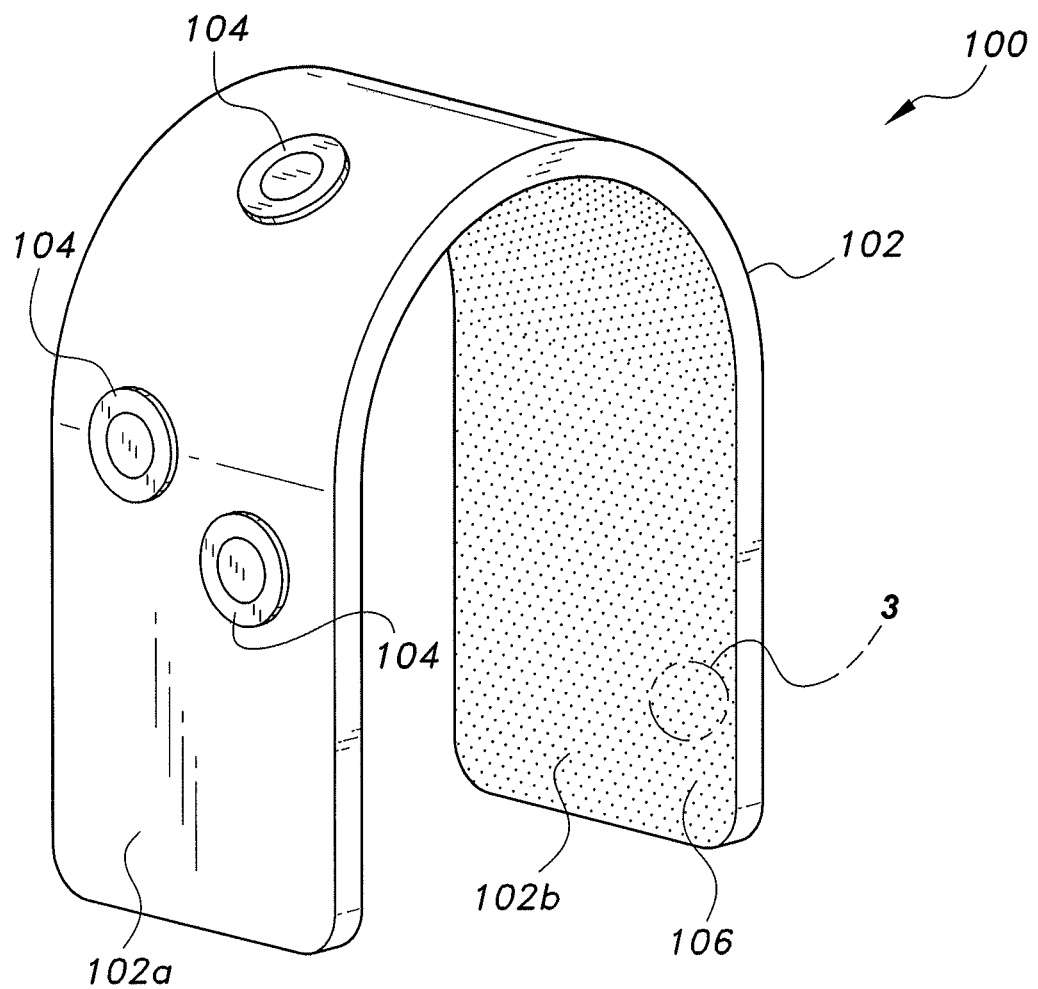
FIG. 2 is a perspective view of the intraoral attachment clip of FIG. 1.

FIG. 2 shows the intraoral attachment clip 100 in a preformed U-shape. A U-shaped clip may be used because of its profile conforming to the edentulous ridge 200. However, since the clip 100 is flexible and shaped by the practitioner, any preformed shape may be used, including a flat sheet.

Figure 3:
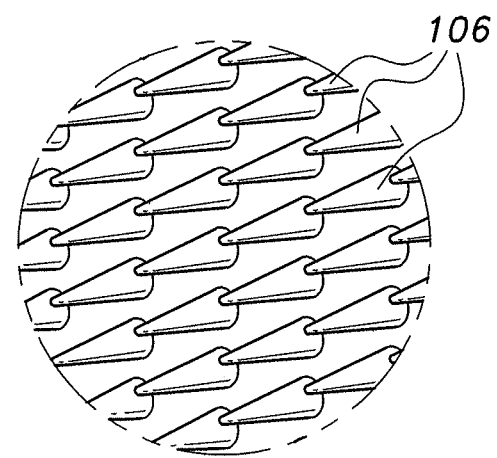
FIG. 3 is a detail view of the area designated as 3 in FIG. 2, showing microprojections on the tissue surface of the clip of FIG. 2.
Figure 4:
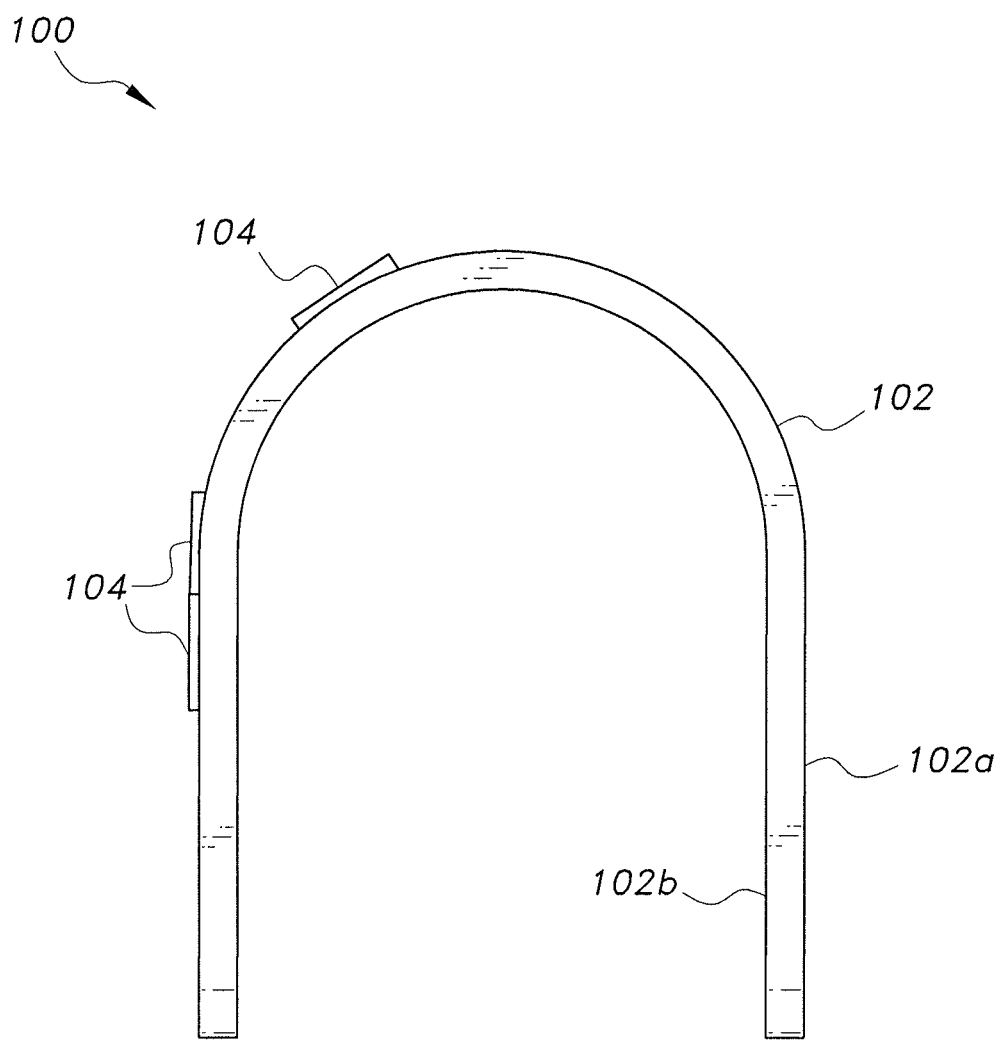
FIG. 4 is a side view of the intraoral attachment clip of FIG. 1.

The clip 100 is held in place by multiple means. First, as discussed above, the clip 100 is formed by the practitioner to conform to the shape of the patient's edentulous ridge 200. Second, as shown in FIG. 3, the tissue surface 102b of the clip 100 has microprojections 106. The microprojections 106 are designed to create a rough surface that will provide greater friction and increase the surface area in contact with the mucosa of the edentulous ridge 200. Finally, an adhesive compatible with oral mucosa is used to bond the lower surface 102b of the clip 100 to the mucosa on the edentulous ridge 200. Through the combination of these attachment means, the clip 100 is capable of being retained in its installed position for greater than a week.

The microprojections 106 are not designed to penetrate the mucosa covering the edentulous ridge 200, but to bear against the mucosa and increase the surface area of the tissue surface 102b of the clip 100 to provide for greater traction to avoid slippage. Accordingly, known techniques for producing roughened or porous surfaces on medical implants may be used to create the microprojections 106. In a preferred embodiment, the micro-projections 106 may have a height in the range of 1 μm to 999 μm. The microprojections 106 may be semispherical, pyramidal, cylindrical, conical, randomly/non-uniformly shaped, or a combination thereof.

The adhesive must be compatible with oral mucosa, must allow firm attachment of the clip 100 to the mucosa, and are preferably dissolved by application of a secondary material for removal of the clip 100 with minimum trauma to the mucosa. An exemplary adhesive is cyanoacrylate. In some embodiments the clip 100 may be prepackaged with the adhesive on the tissue surface 102b. In other embodiments, the clip 100 can be packaged without adhesive applied, thus requiring the practitioner to apply adhesive during installation.

As previously discussed, the clip 100 may be used to secure tracking sensors and/or fiducial markers 104 for use with a surgical navigation system or imaging of the oral region by X-ray or CT scan. Specific tracking sensors and/or fiducial markers 104 can be selected based on the imaging/navigation device being used, the goal of the procedure, and/or the preference of the practitioner. The fiducial markers 104 shown in the drawings are circular. However, any shape may be used. The tracking sensors and/or fiducial markers 104 may be placed on any location of the oral surface 102a of the clip 100. The location of the tracking sensors and/or fiducial markers 104 will typically be chosen based on the same criteria listed above for selecting a marker. Any radiopaque marker material that does not produce severe artifacts in computer tomography may be used for the fiducial markers. Examples of acceptable material include gutta percha, composite restorative materials, radiopaque plastic, and iodine-based contrast agents. The clip 100 is capable of being used with any commercially available guidance system for oral surgery, so long as the necessary tracking sensors and/or fiducial markers can be modified to fit on the clip 100.

Alternative embodiments of the clip 100 can be designed to receive tracking sensors and/or fiducial markers 104 placed by the surgeon. This will allow the practitioner to prepare clips 100 for specific procedures from a standard set of clip bodies 100 and fiducial markers 104.

The clips 100 may also be used to dispense sustained release medication to the patient over a prolonged period of time. For example, a clip 100 that is secured to the patient's edentulous ridge 200 for a surgical guidance procedure may be left in place for multiple days, since the fitting of the marker and the surgical procedure may be on different days. Over this period of time, there may be risks of pain or irritation to the mucosa under the clip 100. To combat these risks, a time-release medication may be incorporated into the clip 100 to release medication through the tissue surface 102b of the clip 100 over the period of time for which the clip is attached. Alternatively, the clip 100 may be used only for dispensing medication. This may be used in situations where it is desired to have a slow release medication without the need for guided surgery or imaging. The medication may be placed across the tissue surface 102b of the clip 100. Alternatively, the medication may be housed inside the clip body 102 with a portion being exposed to the lower surface 102b of the clip 100.

The intraoral attachment clips 100 are designed to be individually packaged in sterile containers. The individually packaged clips 100 may be packaged into kits that include multiple clips 100 of different shapes and sizes for different portion of edentulous ridges 200, different procedures, and/or patients having different size edentulous ridges 200. Different shapes may be useful when the rectangular clip, as shown in the drawings, may be too bulky. For example, if the gap between teeth is not large enough to accept the rectangular clip 100, a clip with a narrow midsection and wide ends may be used. The narrow midsection will fit between the teeth while the wide end sections will provide the surface area necessary for attachment to the edentulous ridge 200 and for securing the fiducial markers 104.

The clip 100 shown in FIG. 1 is designed for use with a surgical navigation system. Multiple fiducial markers 104 are attached to the outer surface 102a of the clip 100 to act as points of reference for the surgical navigation system. A typical surgery using a navigation system may require multiple clips 100 to create a three-dimensional reference grid. Accordingly, multiple clips 100 can be connected on different portions of the maxillary and mandibular edentulous ridges to create the necessary three-dimensional reference grid.

In the case of imaging, the fiducial markers 104 may be used as a scale for measuring. By spacing the fiducial markers 104 a known distance apart on the clip 100, the markers can be used as a reference for size on the produced image.

The clip body 102 may have a body length in the range of 0.5 cm and 4 cm, and a body width in the range of 0.2 cm and 1 cm. As previously discussed, the thickness of the clip body 102 can be determined based on the material and its flexibility.

When attached, the clip 100 is non-invasive or minimally invasive because its attachment does not require damaging any tissue. Since the clip 100 does not damage the surrounding tissue, pain during the period between imaging and surgery is minimized. The clip 100 also minimizes position inaccuracies, since the clip 100 and attached fiducials 104 are left in place from the time of installation through the end of the procedure. The thin profile of the clip 100 allows for the clip 100 to be seated below provisional dentures. The small size of the clip 100 allows for better visibility and accessibility to the surgical field. The small size and intimate contact of the clip 100 reduces the chance of its secured position being shifted relative to the jaw during the procedure.

Installation of the clip 100 may be accomplished through the following steps: selection of a properly dimensioned and configured clip 100; removal of the clip 100 from sterile packaging; application of an adhesive to the tissue surface 102b of the clip 100; placing the clip 100 on the desired portion of the patient's edentulous ridge 200 with a length of the clip running transverse to the ridge 200; conforming the clip 100 to the shape of the edentulous ridge 200 by pushing down on the clip 200 with the practitioner's fingers; and holding the clip 100 against the edentulous ridge 200 until the adhesive sets. The clip 100 will maintain its position for a week or greater, until it is removed by the practitioner. The longevity will allow the practitioner to set the location of the clip 100 on one day and perform the surgery on a later day, or perform multiple surgeries over multiple days using the same reference points for the surgical navigation device. For example, on a first day, the clip 100 can be installed and imaged to produce data for the surgical navigation device. Since several days of surgical planning may separate imaging and the surgical procedure, the clip 100 remains in place so the surgical procedure can be performed on a later day. The clip 100 may be removed by applying an agent that breaks the bond of the adhesive.

During navigation surgeries, tracking sensors that are small enough to be placed inside the mouth may be placed on any location of the oral surface 102a of the clip 100.

It is to be understood that intraoral attachment clip for attachment of objects to edentulous ridges is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An intraoral attachment clip for attachment of objects to edentulous ridges, comprising a body having an oral surface adapted for facing an oral cavity and a tissue surface adapted for abutting mucosal tissues of an edentulous alveolar ridge, the body being a malleable elongated strip, the entirety of the tissue surface having microprojections extending therefrom, the body being dimensioned and configured for extending over the edentulous alveolar ridge and capable of being pressed against the mucosal tissues into close conformity with the ridge, the microprojections reducing slippage against the mucosal tissues.

2. The intraoral attachment clip according to claim 1, further comprising at least one radiopaque fiducial marker mounted on the oral surface for providing guidance for a surgical navigation system.

3. The intraoral attachment clip according to claim 1, wherein the body of the clip is radiolucent.

4. The intraoral attachment clip according to claim 1, further comprising biocompatible adhesive coated on the tissue surface of the body for adhering the body of the clip to the mucosal tissues of the edentulous alveolar ridge.

5. The intraoral attachment clip according to claim 1, wherein the micro-projections have a height between 1 μm and 999 μm.

6. The intraoral attachment clip according to claim 1, further comprising a time-release medication disposed on the tissue surface of the body.

7. The intraoral attachment clip according to claim 1, further comprising at least one tracking sensor mounted on the oral surface for providing tracking for a surgical navigation system.

8. An intraoral attachment clip for attachment of objects to edentulous ridges, comprising a body having an oral surface adapted for facing an oral cavity and a tissue surface adapted for abutting mucosal tissues of an edentulous alveolar ridge, the body being a malleable elongated strip, the tissue surface having a plurality of microprojections extending therefrom, the body being dimensioned and configured for extending over the edentulous alveolar ridge and capable of being pressed against the mucosal tissues into close conformity with the ridge, the microprojections reducing slippage against the mucosal tissues, wherein the tissue surface of the body includes a biocompatible adhesive coated thereon for adhering the body of the clip to the mucosal tissues of the edentulous alveolar ridge.

9. The intraoral attachment clip according to claim 1, further comprising at least one radiopaque fiducial marker mounted on the oral surface for providing guidance for a surgical navigation system.

10. The intraoral attachment clip according to claim 1, wherein the body of the clip is radiolucent.

11. The intraoral attachment clip according to claim 1, wherein the micro-projections have a height between 1 μm and 999 μm.

12. The intraoral attachment clip according to claim 1, further comprising a time-release medication disposed on the tissue surface of the body.

13. The intraoral attachment clip according to claim 1, further comprising at least one tracking sensor mounted on the oral surface for providing tracking for a surgical navigation system.

* * * * *